(12) United States Patent
Gifford et al.

(10) Patent No.: US 7,311,701 B2
(45) Date of Patent: Dec. 25, 2007

(54) METHODS AND APPARATUS FOR NON-INVASIVELY TREATING ATRIAL FIBRILLATION USING HIGH INTENSITY FOCUSED ULTRASOUND

(75) Inventors: Hanson S. Gifford, Woodside, CA (US); Mark Deem, Mountain View, CA (US)

(73) Assignee: Cierra, Inc., Redwood City, CA (US)

( * ) Notice: Subject to any disclaimer, the term of this patent is extended or adjusted under 35 U.S.C. 154(b) by 151 days.

(21) Appl. No.: 10/764,148

(22) Filed: Jan. 23, 2004

(65) Prior Publication Data

US 2005/0228283 A1    Oct. 13, 2005

Related U.S. Application Data

(60) Provisional application No. 60/477,532, filed on Jun. 10, 2003.

(51) Int. Cl.
*A61N 7/00* (2006.01)
(52) U.S. Cl. .............................. 606/27; 128/898; 606/1
(58) Field of Classification Search ................ 128/898; 606/27
See application file for complete search history.

(56) References Cited

U.S. PATENT DOCUMENTS

| 2,275,167 A | 3/1942 | Bierman |
| 2,580,628 A | 1/1952 | Welsh |
| 2,888,928 A | 6/1959 | Seiger |
| 3,490,442 A | 1/1970 | Streu |
| 3,862,627 A | 1/1975 | Hans, Sr. |
| 3,874,388 A | 4/1975 | King et al. |
| 3,906,955 A | 9/1975 | Roberts |
| 4,307,720 A | 12/1981 | Weber, Jr. |
| 4,326,529 A | 4/1982 | Doss et al. |
| 4,473,077 A | 9/1984 | Noiles et al. |
| 4,485,817 A | 12/1984 | Swiggett |
| 4,556,065 A | 12/1985 | Hoffmann |
| 4,562,838 A | 1/1986 | Walker |
| 4,682,596 A | 7/1987 | Bales et al. |
| 4,788,975 A | 12/1988 | Shturman et al. |
| 4,798,594 A | 1/1989 | Hillstead |

(Continued)

FOREIGN PATENT DOCUMENTS

EP          135840 A2     4/1985

(Continued)

OTHER PUBLICATIONS

Athiraman et al., "Selective Photothermal Tissue Interaction Using 805-nm Laser and Indocyanine Green in Tissue Welding," *Journal of X-Ray Science and Technology*, vol. 12, No. 2, (2004), pp. 117-126.

(Continued)

*Primary Examiner*—Henry M. Johnson, III
(74) *Attorney, Agent, or Firm*—Townsend and Townsend and Crew LLP; J. Feuchtwang, Esq.

(57) ABSTRACT

Methods and apparatus are provided for non-invasively treating patent foramen ovale using an ultrasound imaging system and a high intensity focused ultrasound system to selectively target high intensity ultrasound energy on either or both of a patient's septum primum or septum secundum.

11 Claims, 3 Drawing Sheets

U.S. PATENT DOCUMENTS

| | | | |
|---|---|---|---|
| 4,832,048 A | 5/1989 | Cohen | |
| 4,884,567 A | 12/1989 | Elliott et al. | |
| 4,895,565 A | 1/1990 | Hillstead | |
| 4,911,159 A | 3/1990 | Johnson et al. | |
| 4,919,129 A | 4/1990 | Weber, Jr. et al. | |
| 4,929,246 A | 5/1990 | Sinofsky | |
| 4,976,711 A | 12/1990 | Parins et al. | |
| 4,986,889 A | 1/1991 | Charamathieu et al. | |
| 5,041,095 A | 8/1991 | Littrell | |
| 5,042,707 A | 8/1991 | Taheri | |
| 5,055,100 A | 10/1991 | Olsen | |
| 5,056,517 A | 10/1991 | Fenici | |
| 5,057,107 A | 10/1991 | Parins et al. | |
| 5,071,417 A | 12/1991 | Sinofsky | |
| 5,071,418 A | 12/1991 | Rosenbaum | |
| 5,078,717 A | 1/1992 | Parins et al. | |
| 5,099,827 A | 3/1992 | Melzer et al. | |
| 5,125,928 A | 6/1992 | Parins et al. | |
| 5,156,608 A | 10/1992 | Troidl et al. | |
| 5,156,613 A | 10/1992 | Sawyer | |
| 5,171,311 A | 12/1992 | Rydell | |
| 5,195,959 A | 3/1993 | Smith | |
| 5,196,007 A | 3/1993 | Ellman et al. | |
| 5,197,963 A | 3/1993 | Parins | |
| 5,207,670 A | 5/1993 | Sinofsky | |
| 5,209,756 A | 5/1993 | Seedhom et al. | |
| 5,290,278 A | 3/1994 | Anderson | |
| 5,292,362 A | 3/1994 | Bass et al. | |
| 5,295,955 A | 3/1994 | Rosen et al. | |
| 5,300,065 A | 4/1994 | Anderson | |
| 5,336,221 A | 8/1994 | Anderson | |
| 5,336,252 A | 8/1994 | Cohen | |
| 5,342,413 A | 8/1994 | Hirschberg et al. | |
| 5,345,935 A | 9/1994 | Hirsch | |
| 5,370,675 A | 12/1994 | Edwards et al. | |
| 5,380,304 A | 1/1995 | Parker | |
| 5,383,917 A | 1/1995 | Desai et al. | |
| 5,405,322 A | 4/1995 | Lennox et al. | |
| 5,409,479 A | 4/1995 | Dew et al. | |
| 5,409,481 A | 4/1995 | Poppas et al. | |
| 5,500,012 A | 3/1996 | Brucker et al. | |
| 5,505,730 A | 4/1996 | Edwards | |
| 5,507,744 A | 4/1996 | Tay et al. | |
| 5,540,677 A | 7/1996 | Sinofsky | |
| 5,569,239 A | 10/1996 | Sinofsky | |
| 5,571,216 A | 11/1996 | Anderson | |
| 5,575,772 A | 11/1996 | Lennox | |
| 5,584,872 A | 12/1996 | Lafontaine et al. | |
| 5,611,794 A | 3/1997 | Sauer et al. | |
| 5,620,481 A | 4/1997 | Desai et al. | |
| 5,626,607 A | 5/1997 | Malecki et al. | |
| 5,662,643 A | 9/1997 | Kung et al. | |
| 5,665,109 A | 9/1997 | Yoon | |
| 5,669,934 A | 9/1997 | Sawyer | |
| 5,693,078 A | 12/1997 | Desai et al. | |
| 5,709,224 A | 1/1998 | Behl | |
| 5,713,891 A | 2/1998 | Poppas | |
| 5,725,522 A | 3/1998 | Sinofsky | |
| 5,730,742 A | 3/1998 | Wojciechowicz | |
| 5,749,895 A | 5/1998 | Sawyer et al. | |
| 5,782,899 A | 7/1998 | Imran | |
| 5,814,065 A | 9/1998 | Diaz | |
| 5,824,015 A | 10/1998 | Sawyer | |
| 5,827,265 A | 10/1998 | Glinsky et al. | |
| 5,846,196 A | 12/1998 | Siekmeyer et al. | |
| 5,855,312 A | 1/1999 | Toledano | |
| 5,871,443 A | 2/1999 | Edwards et al. | |
| 5,919,200 A | 7/1999 | Stambaugh et al. | |
| 5,925,078 A | 7/1999 | Anderson | |
| 5,928,266 A | 7/1999 | Kontos | |
| 5,931,165 A | 8/1999 | Reich et al. | |
| 5,944,738 A | 8/1999 | Amplatz et al. | |
| 5,972,023 A | 10/1999 | Tanner et al. | |
| 5,972,024 A | 10/1999 | Northrup, III et al. | |
| 6,004,316 A | 12/1999 | Laufer | |
| 6,036,699 A | 3/2000 | Andreas et al. | |
| 6,056,760 A | 5/2000 | Koike et al. | |
| 6,063,081 A | 5/2000 | Mulier | |
| 6,063,085 A | 5/2000 | Tay | |
| 6,083,223 A | 7/2000 | Baker | |
| 6,086,570 A | 7/2000 | Aboul-Hosn et al. | |
| 6,086,586 A | 7/2000 | Hooven | |
| 6,087,552 A | 7/2000 | Gregory | |
| 6,132,429 A | 10/2000 | Baker | |
| 6,149,660 A | 11/2000 | Laufer et al. | |
| 6,156,032 A | 12/2000 | Lennox | |
| 6,168,594 B1 | 1/2001 | Lafontaine | |
| 6,211,335 B1 | 4/2001 | Owen et al. | |
| 6,221,068 B1 | 4/2001 | Fried et al. | |
| 6,236,875 B1 * | 5/2001 | Bucholz et al. | 600/407 |
| 6,257,241 B1 | 7/2001 | Wampler | |
| 6,290,674 B1 | 9/2001 | Roue et al. | |
| 6,302,898 B1 | 10/2001 | Edwards et al. | |
| 6,323,037 B1 | 11/2001 | Lauto et al. | |
| 6,325,798 B1 | 12/2001 | Edwards et al. | |
| 6,355,030 B1 | 3/2002 | Aldrich et al. | |
| 6,375,668 B1 | 4/2002 | Gifford et al. | |
| 6,383,198 B1 | 5/2002 | Hamilton | |
| 6,391,048 B1 | 5/2002 | Ginn et al. | |
| 6,391,049 B1 | 5/2002 | McNally et al. | |
| 6,398,779 B1 | 6/2002 | Buysee et al. | |
| 6,398,782 B1 | 6/2002 | Pecor et al. | |
| 6,398,797 B2 | 6/2002 | Bombard et al. | |
| 6,401,720 B1 | 6/2002 | Stevens et al. | |
| 6,409,720 B1 * | 6/2002 | Hissong et al. | 606/27 |
| 6,413,254 B1 * | 7/2002 | Hissong et al. | 606/27 |
| 6,419,669 B1 | 7/2002 | Frazier et al. | |
| 6,423,057 B1 | 7/2002 | He et al. | |
| 6,436,088 B2 | 8/2002 | Frazier et al. | |
| 6,451,013 B1 * | 9/2002 | Bays et al. | 606/27 |
| 6,456,865 B2 | 9/2002 | Samson | |
| 6,458,100 B2 | 10/2002 | Roue et al. | |
| 6,475,213 B1 | 11/2002 | Whayne et al. | |
| 6,482,224 B1 | 11/2002 | Michler et al. | |
| 6,514,250 B1 | 2/2003 | Jahns et al. | |
| 6,558,314 B1 | 5/2003 | Adelman et al. | |
| 6,558,382 B2 | 5/2003 | Jahns et al. | |
| 6,562,037 B2 | 5/2003 | Paton et al. | |
| 6,583,117 B2 | 6/2003 | Owen et al. | |
| 6,584,360 B2 | 6/2003 | Francischelli et al. | |
| 6,589,237 B2 | 7/2003 | Woloszko | |
| 6,606,523 B1 | 8/2003 | Jenkins | |
| 6,641,604 B1 | 11/2003 | Adelman | |
| 6,645,202 B1 | 11/2003 | Pless et al. | |
| 6,645,225 B1 | 11/2003 | Atkinson | |
| 6,648,897 B2 | 11/2003 | Hamilton | |
| 6,652,518 B2 | 11/2003 | Wellman | |
| 6,669,693 B2 | 12/2003 | Friedman | |
| 6,676,685 B2 | 1/2004 | Pedros et al. | |
| 6,682,546 B2 | 1/2004 | Amplatz | |
| 6,692,450 B1 * | 2/2004 | Coleman | 601/3 |
| 6,702,835 B2 | 3/2004 | Ginn | |
| 6,712,804 B2 | 3/2004 | Roue et al. | |
| 6,712,836 B1 | 3/2004 | Berg et al. | |
| 6,716,211 B2 | 4/2004 | Mulier et al. | |
| 6,726,718 B2 | 4/2004 | Carlyle et al. | |
| 6,730,108 B2 | 5/2004 | Van Tassel et al. | |
| 6,733,498 B2 | 5/2004 | Paton et al. | |
| 6,736,810 B2 | 5/2004 | Hoey et al. | |
| 6,755,790 B2 | 6/2004 | Stewart et al. | |
| 6,770,072 B1 | 8/2004 | Truckai et al. | |
| 6,776,784 B2 | 8/2004 | Ginn | |
| 6,790,218 B2 | 9/2004 | Jayaraman | |
| 6,846,319 B2 | 1/2005 | Ginn et al. | |

| | | | | | | |
|---|---|---|---|---|---|---|
| 6,887,238 B2 | 5/2005 | Jahns | | GB | 1260919 | 1/1972 |
| 6,893,431 B2 | 5/2005 | Naimark et al. | | GB | 1550676 | 8/1979 |
| 6,926,716 B2 | 8/2005 | Baker et al. | | GB | 2 359 024 A | 8/2001 |
| 6,929,644 B2 | 8/2005 | Truckai et al. | | WO | WO 85/00018 A1 | 1/1985 |
| 6,932,812 B2 | 8/2005 | Crowley et al. | | WO | WO 87/04081 A1 | 7/1987 |
| 6,946,134 B1 | 9/2005 | Rosen et al. | | WO | WO 90/04352 A1 | 5/1990 |
| 7,025,756 B2 | 4/2006 | Frazier et al. | | WO | WO 91/15996 A1 | 10/1991 |
| 7,165,552 B2 | 1/2007 | Deem et al. | | WO | WO 92/04864 A1 | 4/1992 |
| 2001/0037129 A1 | 11/2001 | Thill | | WO | WO 93/05705 A1 | 4/1993 |
| 2001/0051803 A1 | 12/2001 | Desai et al. | | WO | WO 93/15791 A1 | 8/1993 |
| 2002/0128672 A1 | 9/2002 | Dinger et al. | | WO | WO 94/00178 A1 | 1/1994 |
| 2002/0143322 A1 | 10/2002 | Haghighi | | WO | WO 98/07375 A1 | 2/1998 |
| 2003/0028189 A1 | 2/2003 | Woloszko et al. | | WO | WO 99/18862 A1 | 4/1999 |
| 2003/0045893 A1 | 3/2003 | Ginn | | WO | WO 99/18864 A1 | 4/1999 |
| 2003/0045901 A1 | 3/2003 | Opolski | | WO | WO 99/18870 A1 | 4/1999 |
| 2003/0050665 A1 | 3/2003 | Ginn | | WO | WO 99/18871 A1 | 4/1999 |
| 2003/0065364 A1 | 4/2003 | Wellman et al. | | WO | WO 99/23959 A1 | 5/1999 |
| 2003/0069570 A1 | 4/2003 | Witzel | | WO | WO 99/49788 A * | 10/1999 |
| 2003/0078578 A1 | 4/2003 | Truckai et al. | | WO | WO 00/07506 A2 | 2/2000 |
| 2003/0092988 A1* | 5/2003 | Makin ................. 600/439 | | WO | WO 00/09027 A1 | 2/2000 |
| 2003/0093071 A1 | 5/2003 | Hauck et al. | | WO | WO 01/13810 A1 | 3/2001 |
| 2003/0120268 A1 | 6/2003 | Bertolero et al. | | WO | WO 01/78596 A * | 10/2001 |
| 2003/0144652 A1 | 7/2003 | Baker et al. | | WO | WO 01/78596 A1 | 10/2001 |
| 2003/0144694 A1 | 7/2003 | Chanduszko et al. | | WO | WO 01/82778 A * | 11/2001 |
| 2003/0158551 A1 | 8/2003 | Paton et al. | | WO | WO 03/022159 A1 | 3/2003 |
| 2003/0199868 A1 | 10/2003 | Desai et al. | | WO | WO 03/022160 A1 | 3/2003 |
| 2003/0208232 A1 | 11/2003 | Blaeser | | WO | WO 03/026496 A2 | 4/2003 |
| 2003/0225421 A1 | 12/2003 | Peavey et al. | | WO | WO 03/053493 A2 | 7/2003 |
| 2003/0233091 A1 | 12/2003 | Whayne et al. | | WO | WO 03/071957 A2 | 9/2003 |
| 2004/0059347 A1 | 3/2004 | Hamilton | | WO | WO 03/082076 A2 | 10/2003 |
| 2004/0092973 A1 | 5/2004 | Chanduszko et al. | | WO | WO 03/094742 A1 | 11/2003 |
| 2004/0098031 A1 | 5/2004 | Van der Burg et al. | | WO | WO 2004/019791 A2 | 3/2004 |
| 2004/0098042 A1 | 5/2004 | Devellian et al. | | WO | WO 2004/043266 A2 | 5/2004 |
| 2004/0102721 A1 | 5/2004 | McKinley | | WO | WO 2004/069055 A2 | 8/2004 |
| 2004/0143292 A1 | 7/2004 | Marino et al. | | WO | WO 2004/082532 A1 | 9/2004 |
| 2004/0153057 A1 | 8/2004 | Davison | | WO | WO 2004/091411 A2 | 10/2004 |
| 2004/0153098 A1 | 8/2004 | Chin et al. | | WO | WO 2005/006990 A2 | 1/2005 |
| 2004/0176799 A1 | 9/2004 | Chanduszko et al. | | WO | WO 2005/027753 A1 | 3/2005 |
| 2004/0220596 A1 | 11/2004 | Frazier et al. | | WO | WO 2005/034738 A2 | 4/2005 |
| 2004/0243122 A1 | 12/2004 | Auth | | WO | WO 2005/074814 A2 | 8/2005 |
| 2004/0249398 A1 | 12/2004 | Ginn | | WO | WO 2005/046487 A1 | 12/2005 |
| 2005/0021059 A1 | 1/2005 | Cole et al. | | WO | WO 2005/115256 A | 12/2005 |
| 2005/0033288 A1 | 2/2005 | Auth et al. | | | | |
| 2005/0033327 A1 | 2/2005 | Gainor et al. | | | | |
| 2005/0055050 A1 | 3/2005 | Alfaro | | | | |
| 2005/0065506 A1 | 3/2005 | Phan | | | | |
| 2005/0065509 A1 | 3/2005 | Coldwell et al. | | | | |
| 2005/0070923 A1 | 3/2005 | McIntosh | | | | |
| 2005/0075665 A1 | 4/2005 | Brenzel et al. | | | | |
| 2005/0119675 A1 | 6/2005 | Adams et al. | | | | |
| 2005/0125032 A1 | 6/2005 | Whisenant et al. | | | | |
| 2005/0171526 A1 | 8/2005 | Rioux et al. | | | | |
| 2005/0187568 A1 | 8/2005 | Klenk et al. | | | | |
| 2005/0192626 A1 | 9/2005 | Widomski et al. | | | | |
| 2005/0192627 A1 | 9/2005 | Whisenant et al. | | | | |
| 2005/0192654 A1 | 9/2005 | Chanduszko et al. | | | | |
| 2005/0209636 A1 | 9/2005 | Widomski et al. | | | | |
| 2005/0216054 A1 | 9/2005 | Widomski et al. | | | | |
| 2005/0251201 A1 | 11/2005 | Roue et al. | | | | |
| 2005/0256532 A1 | 11/2005 | Nayak et al. | | | | |
| 2005/0267495 A1 | 12/2005 | Ginn et al. | | | | |
| 2005/0267525 A1 | 12/2005 | Chanduszko | | | | |
| 2006/0036284 A1 | 2/2006 | Blaeser et al. | | | | |
| 2006/0052821 A1 | 3/2006 | Abbott et al. | | | | |
| 2006/0069408 A1 | 3/2006 | Kato | | | | |

FOREIGN PATENT DOCUMENTS

| | | | |
|---|---|---|---|
| EP | | 199694 A2 | 10/1986 |
| EP | | 0265532 A1 | 5/1988 |
| EP | | 0375556 A1 | 6/1990 |
| EP | | 0428812 A1 | 5/1991 |
| EP | | 0947165 A1 | 10/1999 |

OTHER PUBLICATIONS

Fenner et al., "Shear Strength of Tissue Bonds as a Function of Bonding Temperature: A Proposed Mechanism for Laser-Assisted Tissue Welding," *Lasers in Medical Science*, vol. 7, (1992), pp. 39-43.

Godlewski et al., "Applications and Mechanisms of Laser Tissue Welding in 1995: Review," *Proc. SPIE*, vol. 2623, (Jan. 1996) pp. 334-341.

Olson et al., "Developing An Animal Model for the Study of Fusion Using RF Energy," *Proc. SPIE*, vol. 5312, (2004), pp. 147-161.

Ott et al., "Comparative in Vitro Study of Tissue Welding Using a 808 nm Diode Laser and a Ho:YAG laser," *Lasers Med Sci*, vol. 16, (2001) pp. 260-266.

Poppas et al., "Temperature-Controlled Laser Photocoagulation of Soft Tissue: in Vivo Evaluation Using a Tissue Welding Model," Lasers Surg Med., vol. 18, No. 4, (1996), pp. 335-344.

Stewart et al., "Laser Assisted Vascular Welding with Real Time Temperature Control," Lasers Surg Med., vol. 19, No. 1, (1996), pp. 9-16.

Tang et al., "Quantitative Changes in Collagen Levels Following 830-nm Diode Laser Welding," Lasers Surg Med., vol. 22, No. 4, (1998), pp. 207-211.

Tang et al, "Morphologic Changes in Collagen Fibers after 830 nm Diode Laser Welding," Lasers Surg Med., vol. 21, No. 5 (1997), pp. 438-443.

Anzola et al., "Potential Source of Cerebral Embolism in Migraine with Aura," *Neurology* (1999) 52(8): 1622.

De Castro et al., "Morphological and Functional Characteristics of Patent Foramen Ovale and Their Embolic Implications," *Stroke* (Oct. 2002), pp. 2407-2413.

Cordis Corporation, Cordis Ducor® Lumeleo™ Electorode Catheters [brochure], Cordis Corporation, (Dec. 1984), 2 pages.

Del Sette, "Migraine with Aura and Right-to-Left Shunt on Transcranial Doppler: A Case Control Study," *Cerebrovas Dis* (1998) 8:327-330.

Gillette, "Catheter Ablation in Dysrhythmias," *Cardio*, (Mar. 1984), pp. 67-69.

Ho et al., "Morphological Features Pertinent to Interventional Closure of Patent Oval Foramen," *J Interventional Cardiology*, vol. 16 No. 1, (2003), pp. 33-34.

Kennedy et al., "High-burst-Strength, feedback-controlled bipolar vessel sealing," *Surg Endosc* (1998) 12: 876-878.

Koenig et al., "Role of Intracardiac Echocardiographic Guidance in Transcatheter Closure of Atrial Septal Defects and Patent Foramen Ovale Using the Amplatzer® Device," *J. Interventional Cardiology*, (2003) 16 (1):51-62.

Morady, "Transvenous Catheter Ablation of a Posterospetial Accessory Pathway in a Patient with the Wolff Parkinson-White Syndrome," *The New England Journal of Medicine*, (Mar. 15, 1984), 310(11): 705-707.

Morandi et al., "Transcatheter Closure of Patent Foramen Ovale: A New Migraine Treatment?" *J Interventional Cardiology*, (2003), 16(1): 39-42.

Pfleger, "Haemodynamic Quantification of Different Provocation Manoeuvres by Simultaneous Measurement of Right and Left Atrial Pressure: Implications for the Echocardiographic Detection of Persistent Foramen Ovale," *Eur J Echocardiography* (2001) 2: 88-93.

Polgar et al., "A New Technique for Closed-Chest Human His Bundle Ablation Using Suction Electrode Catheter and DC Shock," In: Perez Gomez F, ed. Cardiac Pacing Electrophysiology Tachyarrhythmias. Madrid, Spain: Grouz Publishers; 1985:1582-1586.

Polgar et al., "Comparison of Two Different Techniques for Closed-Chest His Bund*le Ablation,"* In: Perez Gomez F, ed. Cardiac pacing Electrophysiology Tachyarrhythmias. Madrid, Spain: Grouz Publishers; 1985:1578-1587.

Polgar, "Closed Chested Ablation of His Bundle: A New Technique Using Suction Electorde Catheter and DC Shock," *Nachdruck Aus: Cardio Pacing*, (1983), pp. 883-890.

Stuart, "What's All the Flap About PFO Closure?," *Start-Up: Windhover's Review of Emerging Medical Ventures*, (Nov. 10, 2004), pp. 9-14.

Sztajel et al., "Patent Foramen Ovale, a Possible Cause of Symptomatic Migraine: A Study of 74 Patients with Acute Ischemic Stroke," *Cerebrovas Dis* (2002) 13: 102-106.

Thomas, "Patent Foramen Ovale with Right-to-left Shunting: Echocariographic Alternatives," *Eur J Echocariography* (2001) 2:74-75.

Wilmhurst et al., "Effect on Migraine of Closure of Cardiac Right-to-Left Shunts to Prevent Recurrence of Decompression Illness of Illness or Stroke or for Haemodynamic Reasons," *The Lancet*, vol. 356, (Nov. 11, 2000), pp. 1648-1651.

Wilmhurst et al., "Relationship between Migraine and Cardiac and Pulmonary Right to Left Shunts," *Clinical Science* (2001) 100:215-220.

\* cited by examiner

SUMMARY OF THE INVENTION

In view of the foregoing, it is an object of the present invention to provide methods and apparatus for treating PFO so as to cause closure by ablating or applying energy to weld the tissue at a distance from that tissue, so that the procedure may be performed non-invasively.

It is another object of the present invention to provide methods and apparatus for treating PFO by applying energy from outside the body or from neighboring organs, such as the esophagus, that are easily accessible.

These and other objects of the present invention are accomplished by providing methods and apparatus that enable a physician to image tissue within the body that is to be heated or ablated, and then to heat or ablate that tissue using a completely or relatively non-invasive procedure, and with little or no anesthesia. Advantageously, the methods and apparatus of the present invention are expected to be cost-effective and time-efficient to perform compared to the previously-known surgical and interventional procedures.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE INVENTION

The present invention is directed to methods and apparatus for creating lesions in the walls of the heart or for ablating or welding the tissue of a PFO in a non-invasive manner using high intensity focused ultrasound (HIFU). Previously-known HIFU systems, such as those being developed by Epicor Medical or Transurgical, require close approximation of the HIFU device to the target tissue. These systems are not adapted for PFO closure. The methods and apparatus of the present invention overcome this drawback by providing systems that enable the creation of lesions in the heart wall from a greater distance.

Figure 1:
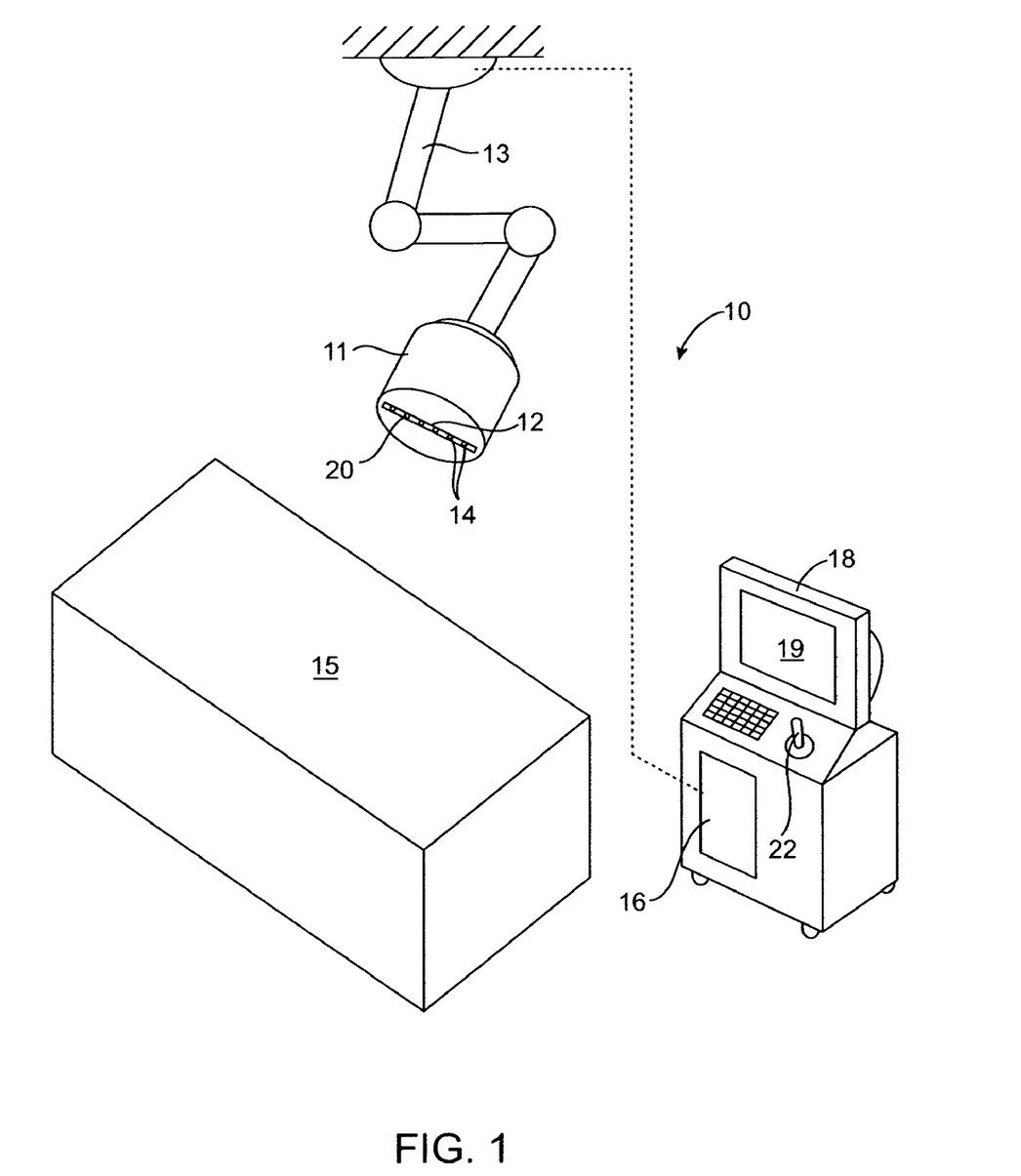
FIG. 1 is a schematic view of an illustrative imaging and treatment ultrasound system of the present invention.

Referring to FIG. 1, apparatus constructed in accordance with the principles of the present invention is described. System 10 comprises head 11 housing ultrasound imaging system 12 and high intensity focused ultrasound energy ("HIFU") system 14. Ultrasound imaging system 12 and HIFU system 14 may have in common all or just a subset of the transducers and related components, operating in different modes to image or ablate. Head 11 is mounted on arm 13 that permits the head to be positioned in contact with a patient (not shown) lying on table 15. Head 11 also may be a handheld unit, not needing an arm 13 to support or position it. System 10 includes controller 16 that controls operation of imaging system 12 and HIFU system 14. Monitor 18 displays images output by imaging system 12 that allows the clinician to identify the desired locations on the walls of the heart to be treated.

Figure 2:
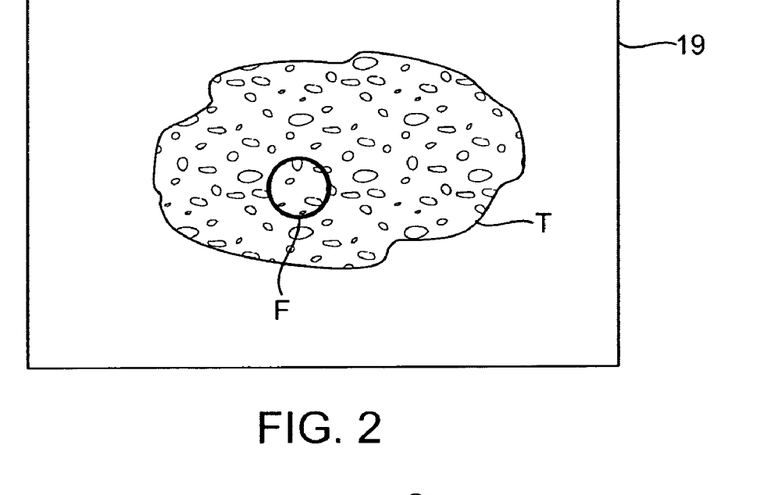
FIG. 2 is a schematic view of an illustrative display of the imaging and treatment ultrasound system of the present invention.

In accordance with the methods of the present invention, controller 16 and monitor 18 also are programmed to indicate the focus of the HIFU energy relative to the image of the tissue cross-section. FIG. 2 shows illustrative screen display 19 of monitor 18 wherein the outline T of the tissue, as imaged by imaging system 12, and a marker corresponding to the location of focal point F of HIFU system 14, may be seen.

When activated, the HIFU system delivers ablative energy to the specific location shown on monitor 18 (focal point F in FIG. 2), thus enabling safe creation of lesions or tissue welds. Because the HIFU system is configured to deliver energy from a number of sources focused towards the target tissue area, intervening tissue is subjected to only a fraction of the energy deposited in the target tissue receives, and thus the intervening tissue is not significantly heated or ablated.

Referring still to FIG. 1, ultrasound imaging system 12 may be similar in design to previously-known trans-thoracic ultrasound imaging systems, and are per se known. High intensity focused ultrasound system 14 may comprise one or more HIFU generators 20 constructed as described in U.S. Patent Publication No. U.S. 20010031922A1. As mentioned before, imaging system 12 and HIFU system 14 also may use common elements. Preferably, each HIFU generator 20 is the same as or is disposed approximately in the same plane as the imaging elements of ultrasound imaging system 12, so that the focus of HIFU system 14 occurs in the plane of the target tissue imaged by ultrasound imaging system 12. In addition, this arrangement advantageously ensures that the HIFU energy will reach the target.

In a preferred embodiment, HIFU generators 20 deliver energy at a frequency optimized for heating myocardium, so that the lesions created will weld, occlude, or lead to the occlusion of the patent foramen ovale. Once the lesions are created, a gradual healing process is begun in which the lesions fibrose, thus permanently sealing the opening.

While it may be possible to image and heat simultaneously, it may occur that the output of HIFU system 14 may interfere with the ability to image the tissue using ultrasound imaging system 12. Accordingly, controller 16 may be programmed to time-gate operation of imaging system 12 and HIFU system 14, so that the tissue is alternately imaged and ablated at a frequency of up to several times per second.

In order to apply energy to the wall of the septa of the heart sufficient to occlude the PFO, it may be desirable to slowly move the focus of the HIFU system along the wall of the septa during the ablation process. While this may be accomplished by manually moving the HIFU system, it may alternatively be desirable to automate the process. For example, controller 16 may include suitable programming and joystick 22, or other input device, for refocusing the focal point of HIFU system 14 along a desired trajectory.

Figure 3:
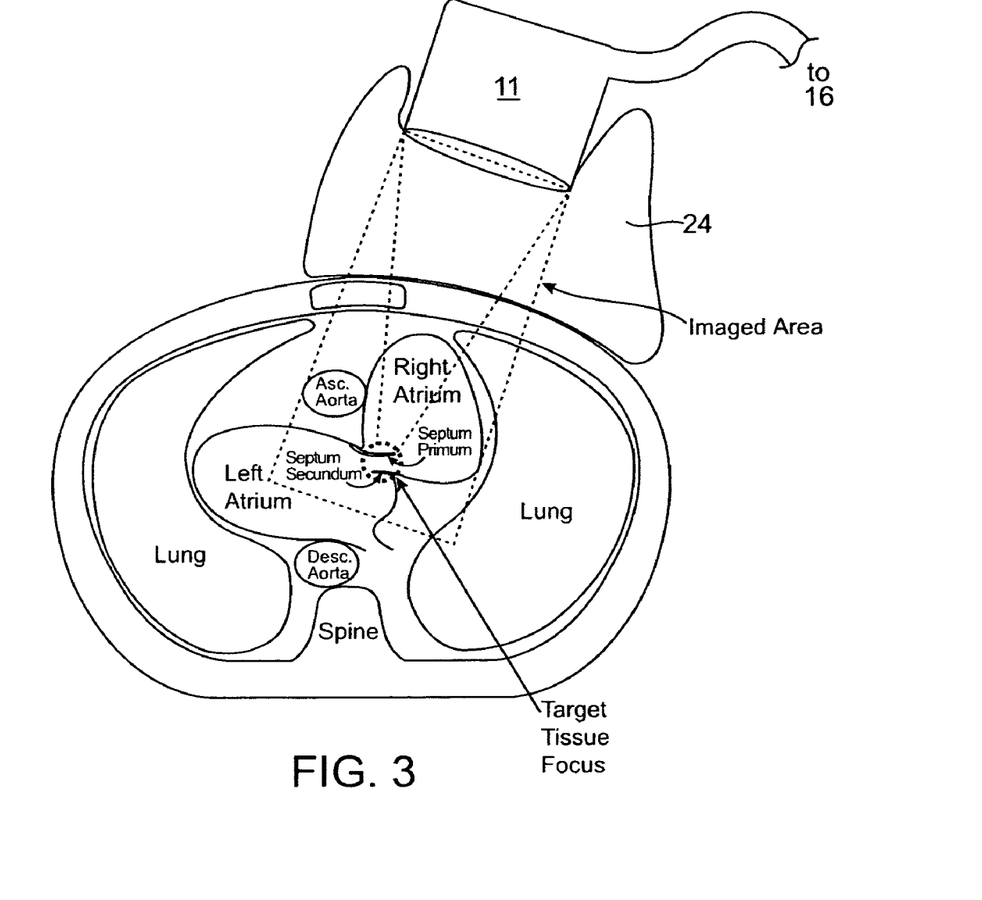
FIG. 3 is a schematic view showing the imaging and treatment ultrasound system of FIG. 1 disposed adjacent to a cross-section of a patient's thorax.

Referring now to FIG. 3, according to an aspect of the present invention, an exemplary method of using the HIFU system to treat PFO is described. More particularly, the HIFU system is used to create localized tissue heating of the septum primum and septum secundum that will lead to occlusion of a PFO. The consequent healing process is expected to cause the septum primum and septum secundum to heal together, thereby permanently closing the PFO or resulting in acute welding of the tissues. Even if this non-invasive treatment were to be effective in closing PFO in only a small percentage of cases, the procedure would likely become the first choice for use in initial therapy.

The tissues of the septum primum and the septum secundum preferably are in contact when the energy is applied to facilitate welding of the PFO. In cases where heat is applied to cause closure through scar formation and subsequent healing, it is also desirable to have the tissue in apposition to ensure that the correct target tissues are heated to an adequate degree to cause tissue damage. Adequate apposition exists in many patients in the absence of an elevated right atrial pressure. However, in some cases it may be necessary or desirable to artificially increase the pressure gradient between the right and left atria to ensure closure of the PFO and/or to increase the contact pressure between the septum primum and septum secundum.

Closure of the PFO or increased contact pressure between the septum primum and septum secundum can be achieved noninvasively through a variety of known techniques using medications, mechanical expedients, or a combination of the two. By way of example, briefly applying external pressure to a patient's jugular veins will temporarily limit blood flow into the superior vena cava and hence the right atrium. Of course, this lowers the right atrial pressure relative to the left atrial pressure, thereby creating the desired closure or increase in contact pressure. Alternatively, the desired closure or increase in contact pressure may be achieved by administering drugs that increase the patient's blood pressure by increasing heart rate and/or peripheral resistance. One suitable drug for increasing heart rate is epinephrine. As a further alternative, such drugs may be administered in combination with the application of pressure to the patient's jugular veins.

In the system shown in FIG. 3 the focus of the HIFU system is fixed at a certain point within the field of the ultrasound image. For example, the ultrasound image might show a picture of rectangular planar cross-section of tissue with a fixed focus of the HIFU energy in the center of the field. In operation, the clinician manually moves the probe until the desired tissue is in the target area, and then fires the HIFU system to ablate the tissue and occlude or weld the PFO. In order to ablate tissue located less than 130 mm below the skin and still retain a continuous fluid path from the probe to the target, the HIFU system includes fluid-filled balloon 24 that covers the face of the probe.

Balloon 24 preferably is filled with water and enables the clinician to reposition the probe at a variable distance from the skin. Balloon 24 also permits the clinician to position the probe at any desired angle to target tissue not aligned directly under the focal point of HIFU system 14. Alternatively, the patient could sit in a tub of water, so the patient's chest and the probe were both underwater, again ensuring a continuous fluid path.

As a further alternative, controller 16 may be programmed so that the depth of the focal point of the HIFU system is depth-adjustable relative to the imaged tissue. Advantageously, the depth of the targeted tissue then could be adjusted relative to the imaged field, so a smaller fluid-filled balloon, or no balloon, is used to maintain fluid contact while adjusting the angle of the imaged section or make minor changes in the depth of the targeted tissue. WIPO Patent Publication No. WO/0145550A2 to Therus describes several ways to adjust the depth of the focused energy by changing the radius of curvature of one or more of the ultrasound generators. Alternatively, the direction of several focused energy generators of relatively fixed focal length could be shifted relative to one another to move the focal point.

In accordance with the principles of the present invention, focused energy is applied from outside the patient's body. Because ultrasound energy does not travel coherently through non-fluid filled tissue, such as the lungs, positioning of the ultrasound imaging system and HIFU system at certain angles may be more advantageous for treatment of specific areas of the heart.

Accordingly, it may be desirable to locate the imaging system and HIFU system on a movable arm or to position it by hand so as to permit other external approaches, such as from below the diaphragm on the left anterior side of the body, so the ultrasound has a coherent path through the diaphragm and apex and ventricles of the heart to the septa. Application of the probe also may be made along a patient's back.

Figure 4:
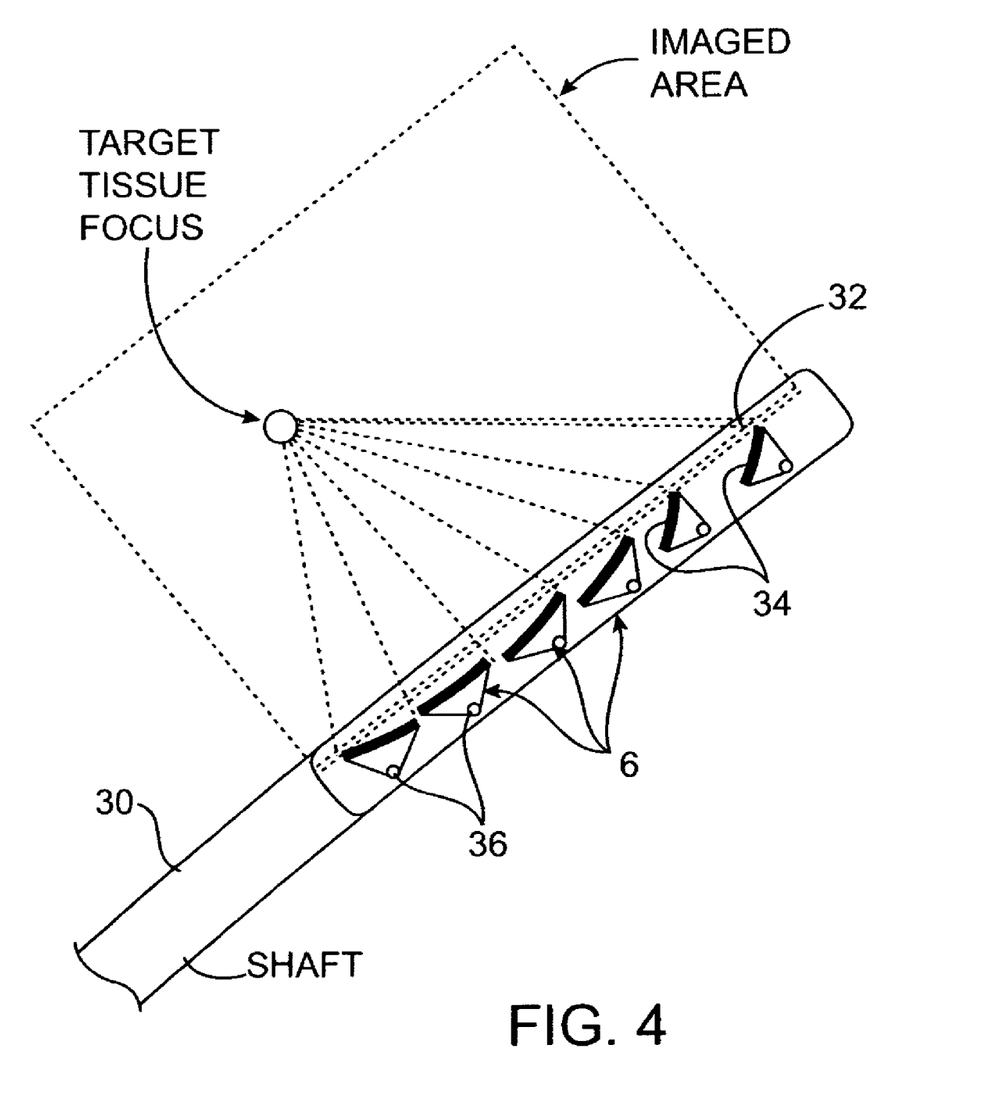
FIG. 4 is a schematic view of the distal region of a catheter-based high intensity focused ultrasound array.

While in the preferred embodiment described hereinabove energy is delivered from outside the body, situations may arise where it is difficult to deliver the energy to the PFO tissue. Referring now to FIG. 4, and in accordance with another aspect of the present invention, methods and apparatus are provided for positioning a probe inside the body and closer to the targeted tissue, but still not necessarily adjacent to it. Intraluminal probe 30 is configured to deliver HIFU energy to the heart from the esophagus, from the aorta, or from the great veins of the heart such as the inferior vena cava, superior vena cava, or the right atrium itself.

This approach is fundamentally different from previously-known methods of performing ablation during surgical procedures using epicardial probes or during interventional procedures using intracardiac ablation catheters. These previously-known devices are designed to be in direct contact or at least very close proximity (e.g., within 5 mm) of the target tissue, and are not designed to avoid ablation of intervening tissue between the probe and the target tissue.

Still referring to FIG. 4, catheter 30 preferably has a diameter in a range of 5 to 10 mm for vascular devices, and a diameter in a range of 5 to 20 mm for an esophageal device. Imaging elements 32 and HIFU elements 34 are arranged linearly along the longitudinal axis of the catheter.

The linear nature of the imaging element and HIFU element array may impose limitations on the ability to reposition the device. While translation and rotation of the catheter may be relatively easy, it is contemplated that it may be difficult to move the device very far to one side or another within a relatively small-diameter body lumen.

Accordingly, intraluminal catheter 30 preferably is configured to adjust the focal point of the HIFU system with respect to both longitudinal position and depth. This may be accomplished by programming the controller used with intraluminal catheter 30 to adjust the focal point of the HIFU system, as described above. Alternatively, refocusing of the array of HIFU elements may be achieved by locating individual HIFU elements on independently steerable actuators 36. Actuators 36 are controlled by the system controller and permit the clinician to move the focal point of the HIFU array to any desired point in the field of view of the imaging system.

In accordance with another aspect of the present invention, methods of using intraluminal catheter 30 to heat or ablate septal tissues from the esophagus to treat PFO are described. The esophagus is separated from the PFO by only about 20-25 mm, such that a lesion may be easily made in the PFO using a probe capable of delivering energy at a distance of approximately 20-50 mm.

As described above, intraluminal catheter 30 preferably is configured, either mechanically or by suitable software algorithms, to move its focal point to enable a continuous linear ablation or heat affected zone without moving the device. Alternatively, the HIFU array of the catheter may be configured to create a linear ablation or heat affected zone, or have a fixed-focus so that a linear ablation or heat affected zone may be created by translating the HIFU array within the esophagus.

In addition, it may be beneficial to cool tissue surrounding the HIFU array of intraluminal catheter 30, to further reduce the risk of damage to the esophagus. Intraluminal catheter 30 may therefore include a water jacket that circulates fluid around the HIFU array to prevent any heat generated by the array or ultrasound energy absorbed by the esophagus from causing any tissue damage.

Although preferred illustrative embodiments of the present invention are described above, it will be evident to one skilled in the art that various changes and modifications may be made without departing from the invention. It is intended in the appended claims to cover all such changes and modifications that fall within the true spirit and scope of the invention.

What is claimed is:

1. A method of treating patent foramen ovale comprising:
    providing a catheter having a distal portion housing an ultrasound imaging system and a high intensity focused ultrasound system disposed in alignment with the ultrasound imaging system;
    disposing the distal portion of the catheter within a patient's body lumen;
    operating the ultrasound imaging system to generate an image of a portion of cardiac tissue; and
    operating the high intensity focused ultrasound system, guided by the image, to heat or ablate either or both of the patient's septum primum or septum secundum.

2. The method of claim 1, wherein the body lumen is the aorta.

3. The method of claim 1, wherein the body lumen is the right atrium.

4. The method of claim 1, wherein the body lumen is the inferior vena cava.

5. The method of claim 1, wherein the body lumen is the superior vena cava.

6. The method of claim 1 further comprising generating and displaying a marker corresponding to a focal point of the high intensity focused ultrasound system on the image.

7. The method of claim 1 further comprising modifying a location of the treatment by adjusting a location of a focal point of the high intensity focused ultrasound system.

8. The method of claim 7 wherein the location of the focal point of the high intensity focused ultrasound system is adjusted within a two-dimensional plane orthogonal to an axis of the high intensity focused ultrasound system.

9. The method of claim 7 wherein the location of the focal point of the high intensity focused ultrasound system is adjusted by modifying a location of a depth of the focal point of the high intensity focused ultrasound system.

10. The method of claim 1 further comprising apposing the patient's septum primum and septum secundum noninvasively using drugs, noninvasive procedures, or a combination thereof.

11. The method of claim 1 further comprising increasing contact pressure between the patient's septum primum and septum secundum is noninvasively using drugs, noninvasive procedures, or a combination thereof.

* * * * *